United States Patent
Effenberger et al.

(10) Patent No.: US 11,291,531 B2
(45) Date of Patent: Apr. 5, 2022

(54) CARTRIDGE FOR STORING, DISCHARGING AND APPLYING A DENTAL COMPOUND

(71) Applicant: Muhlbauer Technology GmbH, Hamburg (DE)

(72) Inventors: Steffen Effenberger, Hamburg (DE); Axel Nowak, Hamburg (DE)

(73) Assignee: Muhlbauer Technology GmbH, Hamburg (DE)

( * ) Notice: Subject to any disclaimer, the term of this patent is extended or adjusted under 35 U.S.C. 154(b) by 43 days.

(21) Appl. No.: 16/324,847

(22) PCT Filed: Aug. 8, 2017

(86) PCT No.: PCT/EP2017/070048
§ 371 (c)(1),
(2) Date: Feb. 11, 2019

(87) PCT Pub. No.: WO2018/029185
PCT Pub. Date: Feb. 15, 2018

(65) Prior Publication Data
US 2019/0167390 A1    Jun. 6, 2019

(30) Foreign Application Priority Data

Aug. 12, 2016 (DE) .......................... 202016004926.8

(51) Int. Cl.
*A61C 9/00* (2006.01)
*A61C 19/06* (2006.01)
(Continued)

(52) U.S. Cl.
CPC .............. *A61C 9/0026* (2013.01); *A61C 5/62* (2017.02); *A61C 5/66* (2017.02); *A61C 9/0033* (2013.01);
(Continued)

(58) Field of Classification Search
CPC ....... A61C 9/0026; A61C 9/0033; A61C 5/66; A61C 5/62; A61C 19/063; A61J 1/00; A61M 2005/341
(Continued)

(56) References Cited

U.S. PATENT DOCUMENTS

| 5,336,088 A | 8/1994 | Discko, Jr. |
| 5,626,473 A * | 5/1997 | Muhlbauer ............ A45D 40/02 |
| | | 433/89 |

(Continued)

FOREIGN PATENT DOCUMENTS

| DE | 1809613 | 6/1970 |
| DE | 699 15 373 | 7/2004 |

(Continued)

OTHER PUBLICATIONS

International Search Report and Written Opinion for PCT/EP2017/070048, dated Oct. 4, 2017, with English translation, 21 pages.

*Primary Examiner* — Heidi M Eide
*Assistant Examiner* — Drew S Folgmann
(74) *Attorney, Agent, or Firm* — Casimir Jones, S.C.; Brian F. Bradley

(57) ABSTRACT

The invention relates to a cartridge for storing, discharging and applying a dental compound, in particular a paste for preparing and drying the gingival sulcus (sulcus gingivae) during dental impression taking. The invention relates to a cartridge (1) for storing, discharging and applying a dental compound, comprising a container (2), which has a hollow chamber (4) for accommodating the dental compound, and a cannula (3). The hollow chamber (4) comprises an outlet opening (5) and an actuator opening (6) opposite the outlet opening (5), and the cannula (3) is fluid-connected to the outlet opening (5), is arranged on the container (2) and is straight in the starting state. The cartridge is characterised in that the cannula (3) is made of plastic and is plastically (Continued)

Figure 1:
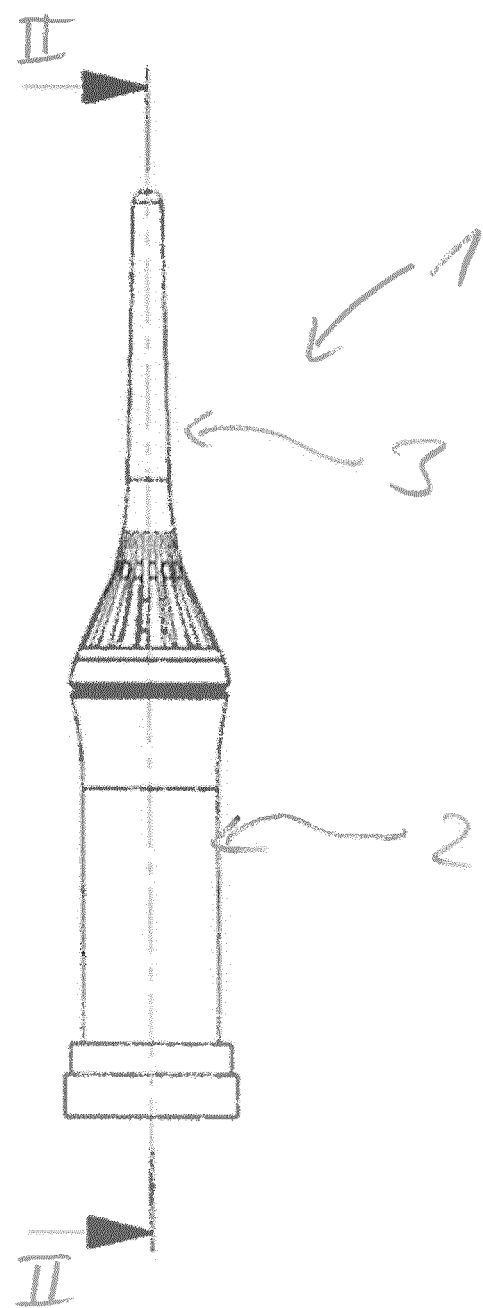

deformable under standard conditions with the application of manual force in such a manner that a permanent bend by an angle of at least up to 65° in comparison with the starting state can be achieved without buckling the cannula (3).

14 Claims, 3 Drawing Sheets

(51) Int. Cl.
    *A61C 5/66*         (2017.01)
    *A61C 5/62*         (2017.01)
    *A61J 1/00*          (2006.01)
    *A61M 5/34*        (2006.01)

(52) U.S. Cl.
    CPC ............... *A61C 19/063* (2013.01); *A61J 1/00* (2013.01); *A61M 2005/341* (2013.01)

(58) Field of Classification Search
    USPC .................................................. 222/526, 527
    See application file for complete search history.

(56) References Cited

U.S. PATENT DOCUMENTS

| | | |
|---|---|---|
| 6,083,002 A | 7/2000 | Martin et al. |
| 6,095,813 A | 8/2000 | Broyles |
| 6,095,814 A | 8/2000 | Petrich et al. |
| 8,616,879 B2 | 12/2013 | Dubey et al. |
| 8,882,502 B2 | 11/2014 | Pauser et al. |
| 2009/0130449 A1* | 5/2009 | El-Siblani ............. G03F 7/0037 |
| | | 428/409 |
| 2012/0077142 A1 | 3/2012 | Mauer et al. |
| 2015/0112251 A1 | 4/2015 | Maclaughlan et al. |
| 2016/0151134 A1* | 6/2016 | Britt ..................... A61C 19/063 |
| | | 433/215 |

FOREIGN PATENT DOCUMENTS

| | | |
|---|---|---|
| DE | 10 2012 202693 | 8/2013 |
| DE | 10 2013 106 716 | 12/2014 |
| JP | 2009-125341 | 6/2009 |

\* cited by examiner

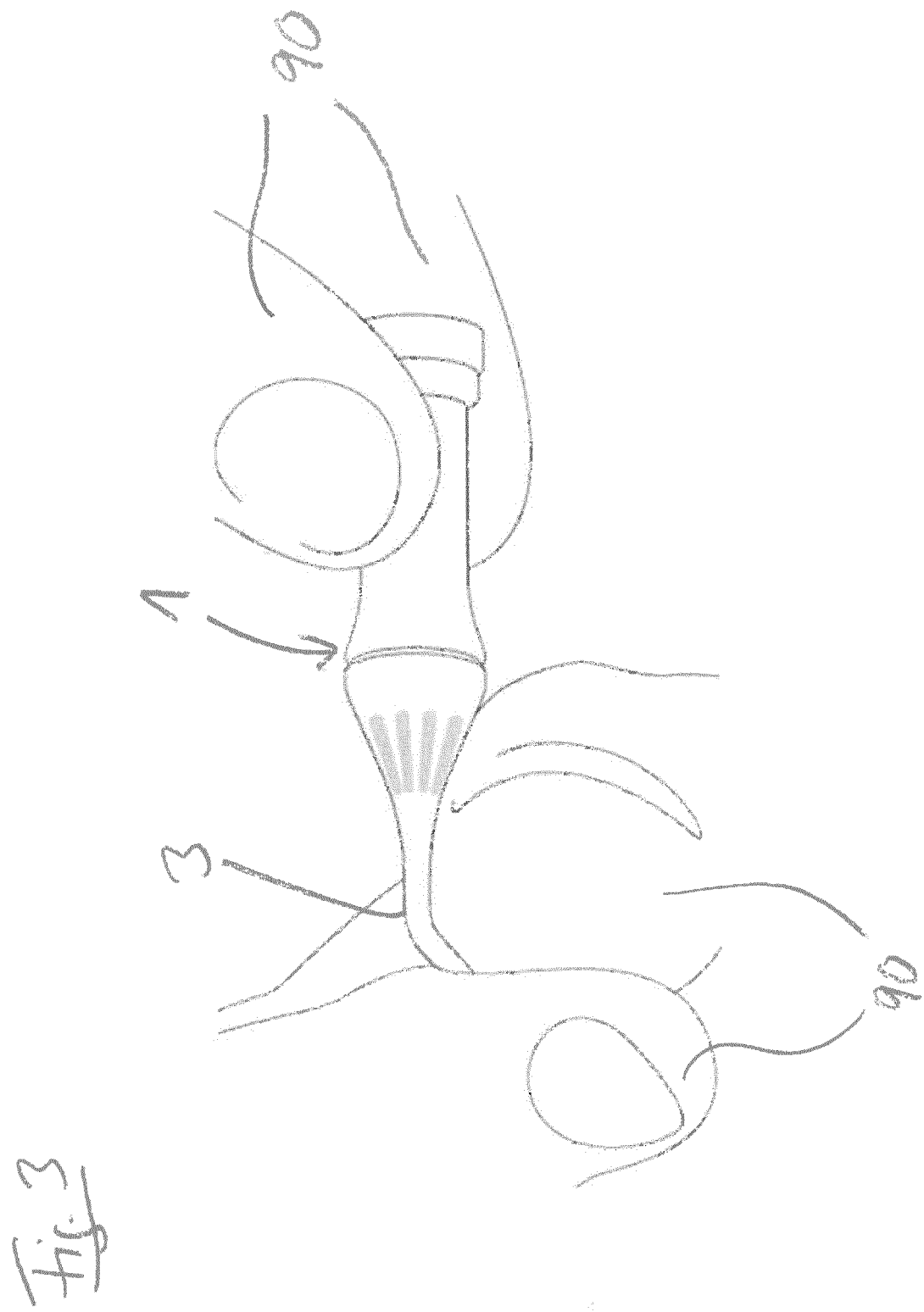

CARTRIDGE FOR STORING, DISCHARGING AND APPLYING A DENTAL COMPOUND

The invention relates to a cartridge for storing, discharging and applying a dental compound, in particular a paste for preparing and drying the gingival sulcus (sulcus gingivae) during dental impression taking.

Various pastes for expanding the gingival sulcus are known in the prior art. In addition to low- and medium-viscosity materials, high-viscosity materials, especially those based on clay minerals, are also known. By virtue of their consistency and high viscosity, corresponding pastes can be inserted deep into the gingival sulcus, against the resistance of the gum tissue, in order to push the gum tissue away from the tooth and keep it away from the latter for the required period of time. A corresponding paste is described in US 2012/077142 A1, for example.

Various devices and systems are already known in the prior art for discharging and applying high-viscosity pastes. The paste containers used in this context generally contain only a single dose and it must accordingly be possible to produce them inexpensively and in a simple manner. At the same time, simple, quick and safe use must be ensured. More particularly, it must be possible to store the paste at room temperature for at least 6 months, preferably 12 or 24 months, without compromising safe use. In particular, the material properties of the paste must not change.

For the safe use of devices for discharging and applying high-viscosity pastes in the dental sector, it is furthermore necessary to keep the squeezing forces as low as possible. At the same time, the containers used must withstand the pressures which arise during squeezing.

U.S. Pat. No. 8,616,879 discloses a system for dispensing a paste, in which a cylindrical container is closed on one side by a piston and on the other side by a removable cap. Before use, the cap must be removed and a metal cannula secured on the container by means of a screwed joint. The use of a corresponding system requires several hand movements. Moreover, production costs are high for systems with a screwed joint.

U.S. Pat. Nos. 6,095,814 and 8,882,502 disclose devices for dispensing high-viscosity pastes in which a rigid cannula is formed directly on a cylindrical container. Here, the container and the cannula are manufactured from plastic. In order to facilitate the ultimate use of the container with the cannula formed thereon, the cannula is preferably arranged at an angle to the axis of the cylindrical container—e.g. 45° in U.S. Pat. No. 8,882,502 or 60° in U.S. Pat. No. 6,095,814. Owing to the arrangement of the cannula at an angle relative to the cylindrical container, production of the corresponding devices is expensive.

It is the underlying object of the invention to create a cartridge for storing, discharging and applying a dental compound in which the disadvantages from the prior art no longer occur or occur only to a reduced extent.

This object is achieved by a cartridge in accordance with the main claim. Advantageous developments form the subject matter of the dependent claims.

Accordingly, the invention relates to a cartridge for storing, discharging and applying a dental compound, comprising a container, which has a hollow chamber for accommodating the dental compound, and a cannula, wherein the hollow chamber comprises an outlet opening and an actuator opening opposite the outlet opening, and the cannula is arranged on the container in such a way as to be fluid-connected to the outlet opening, and is straight in the initial state, wherein the cannula is made of plastic and is plastically deformable in such a manner under standard conditions, with the application of manual force, that a permanent bend by an angle of at least up to 65° in comparison with the initial state can be achieved without buckling of the cannula.

First of all, a number of terms used in the context of the invention will be explained.

A cannula is plastically deformable "with the application of manual force" if no special tools or the like are required for deformation and the bend can in the present case be achieved solely by means of the hands or—based on the typical size of cartridges for storing, discharging and applying dental compounds—by means of individual fingers. Here, a person is assumed to have average capabilities.

A "permanent bend" is the bend due to plastic deformation which remains in the cannula after the removal of the bending forces—i.e. the application of manual force. The angle of the bend corresponds to the angle between the two tangents to both sides of the bend after the removal of the bending forces.

The bending of the cannula takes place without buckling if the curvature of the cannula is constant after bending. In particular, there are no dents in the cannula wall that could restrict the internal cross section of the cannula provided for the passage of the dental compound. The change in the area of the internal cross section—i.e. of the cross section provided for the flow of the dental compound—due to the bend is preferably no more than 10%, preferably no more than 5%.

A paste counts as "highly viscous" if it has a dynamic viscosity of over 27,000 Pa s at a shear stress of 9,000 N/m$^2$ and a shear rate of 0.3 1/s at a temperature of 23° C.

The cartridge according to the invention is distinguished by simple production and simple and, especially, flexible use. Since the cannula can be bent over a wide range, a user can adapt the cannula according to the respective requirements and their personal preferences. Moreover, the cannula can be produced in a simple manner since it is straight in the initial state.

It is preferred if the bend in the cannula is reversed as the dental compound is dispensed from the hollow chamber with a squeezing force of less than 130 N, preferably of less than 150 N, further preferably of less than 200 N only by no more than 10°, preferably by no more than 5°, further preferably being reversed by no more than 1°. In order to achieve this, a person skilled in the art can suitably match the shape and/or material of the cannula to the respective dental compound. A corresponding process of matching the shape and/or material of the cannula is generally required since the restoring force acting on the cannula, in addition to the squeezing force, is decisively dependent on the flow properties of the dental compound, but does not present a person skilled in the art with any problems. The restoring movement during the dispensing of the respective dental compound can likewise be readily determined by appropriate testing.

It is preferred if, at 23° C., the plastic of the cannula has a bending modulus of from 2.2 to 2.9 GPa, preferably of from 2.3 to 2.6 GPa, preferably of about 2.4 GPa, in accordance with DIN EN ISO 178:2013. A corresponding bending modulus is advantageous for the desired manner of functioning of the cannula.

It is preferred if the outlet opening and the actuator opening of the hollow chamber lie on a common axis. As a further preference, the cannula also extends parallel to or along the axis in the initial state. Appropriate arrangement of the outlet opening and of the actuator opening of the hollow chamber and, where appropriate of the cannula in the initial state allows simple production of the cartridge according to the invention.

The cannula is preferably formed integrally with the container. In this case, the entire cartridge can be produced in a single operation. For example, the cannula can be produced together with the container by 1-component or multicomponent injection molding.

It is preferred if the cannula and/or the container is made from a thermoplastic, preferably a substantially amorphous thermoplastic copolymer, terpolymer and/or quadropolymer, further preferably a partially cross-linked, substantially amorphous thermoplastic copolymer, terpolymer or quadropolymer, further preferably from acrylonitrile butadiene styrene (ABS). Corresponding materials have proven fundamentally suitable for the cannula according to the invention.

The thermoplastic preferably contains pigments and/or fillers, wherein the proportion of pigments and/or fillers is preferably less than 50% by weight, further preferably less than 30% by weight.

The cartridge according to the invention is preferably designed for use with a standard dispenser. In addition to the cartridge dimensions required in this case for a standard dispenser, maximum values for the specified actuator and/or squeezing force are thereby also predetermined. For a standard dispenser, the actuator and/or squeezing force is no more than 200 N.

A piston can be provided in the hollow chamber, said piston being arranged in such a way in the initial state of the cartridge that the dental compound can be accommodated in the hollow chamber between the piston and the outlet opening. Providing a corresponding piston matched to the hollow chamber ensures that a dental compound arranged in the hollow chamber can be dispensed completely through the outlet opening. In particular, it is possible to avoid dental compound from forcing its way around the side of the plunger of a dispenser which may not be matched to the hollow chamber of the cartridge and being able in this way to escape at the actuator opening of the cartridge.

It is preferred if the outlet opening of the cannula has an inside diameter of from 0.4 mm to 2 mm, preferably 0.6 mm to 0.9 mm, wherein the outlet end of the cannula is preferably rounded, preferably with a radius of from 0.5 mm to 1.5 mm. A corresponding inside diameter allows the introduction of high-viscosity pastes into a gingival sulcus (sulcus gingivae). The risk of injury to the gum tissue can be reduced by rounding the outlet end.

The flexible region of the cannula preferably has a length of from 15 mm to 25 mm, preferably about of 20 mm. A corresponding length is sufficient to achieve the desired flexibility without buckling. It is simultaneously ensured that the tip of the cannula does not project unnecessarily far from the device for dispensing the dental compound—e.g. a standard dispenser—which could make handling more difficult.

The container is preferably substantially tubular, has an outside diameter of from 6 mm to 7 mm, preferably of from 6.2 mm to 6.6 mm, and has a wall thickness of at least 0.5 mm, preferably at least 0.9 mm and/or a wall thickness of less than 1.5 mm, preferably less than 1.0 mm. The stated properties of the container can be combined in any desired manner here.

The container preferably has an annular enlargement of the outside diameter in the region of the outlet opening and/or of the actuator opening. The stability of the cannula can be increased by means of corresponding enlargement(s).

The cartridge according to the invention is suitable for high-viscosity pastes with a dynamic viscosity of over 27,000 Pa s, preferably at a shear stress of 9,000 N/m$^2$, a shear rate of 0.3 1/s and a temperature of 23° C. In particular, the aqueous astringent retraction pastes containing clay minerals and corrosive astringents (e.g. 20% water, 64% clay mineral (e.g. kaolin), 15% $AlCl_3 x 6H_2O$ and 1% additives) can be stored, discharged and applied. Here, the squeezing force required for discharge and application can be limited to below 200 N. The cartridge therefore preferably comprises a dental compound arranged in the hollow chamber of the container, wherein the dental compound is preferably an astringent retraction paste—e.g. the paste described above. The proportion of fillers present in the dental compound in addition to a liquid can be greater than 50% by weight. The dental compound can contain a strong acid ($pK_s \leq 2$), in particular HCl.

Figure 2:
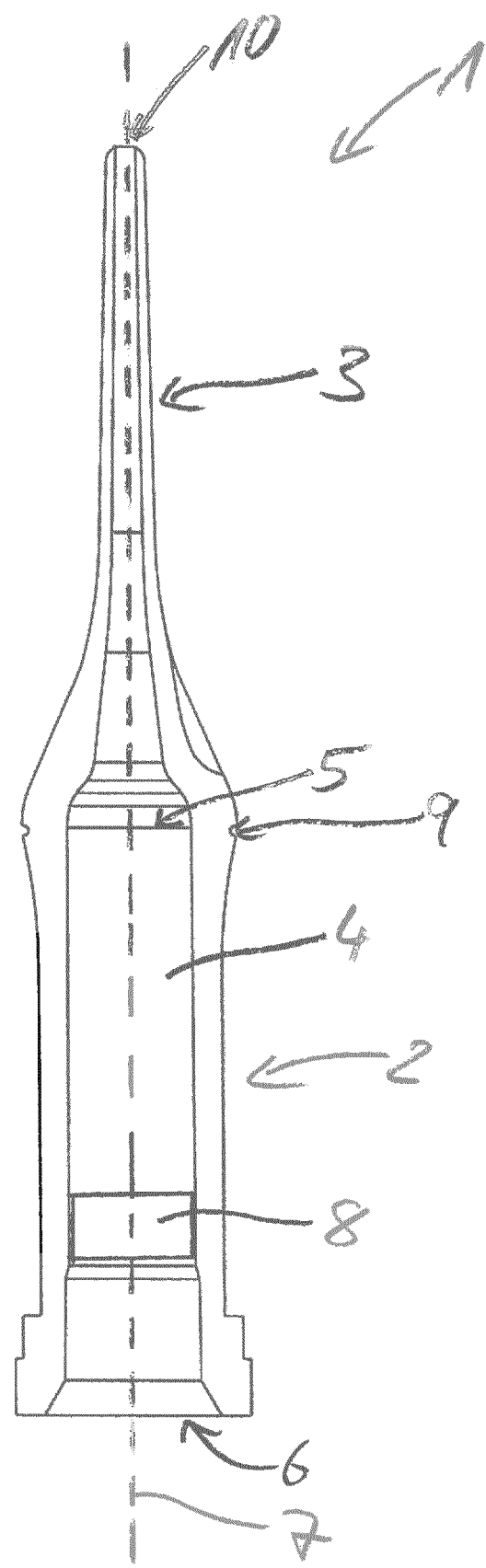

The invention will now be described by way of example by means of an advantageous embodiment with reference to the attached drawings. In the drawings:

FIG. 1: shows a first illustrative embodiment of a cartridge according to the invention;

FIG. 2: shows a sectional view of the cartridge shown in FIG. 1; and

FIG. 3: shows a schematic illustration of the manual bending of the cannula of the cartridge shown in FIGS. 1 and 2.

A first illustrative embodiment of a cartridge 1 according to the invention is illustrated in FIGS. 1 and 2. The cartridge 1 comprises a container 2 and a cannula 3, wherein the cannula 3 is connected permanently to the container 2. In the illustrative embodiment shown, the container 2 and the cannula 3 are formed integrally with one another and are produced in a single operation by 1-component injection molding. The plastic used for the production of the cannula 1 in the illustrative embodiment shown is acrylonitrile butadiene styrene (ABS) with a bending modulus of 2. GPa at 23° C.

The container 2 is of tubular configuration and comprises a hollow chamber 4 for accommodating a dental compound (not shown). The hollow chamber 4, in turn, comprises an outlet opening 5 and an actuator opening 6, which are arranged on a common longitudinal axis 7. Arranged in the hollow chamber 4 is a piston 8, which, in the illustrated initial state of the cartridge 1, is arranged close to the actuator opening 6, enabling the dental compound situated in the hollow chamber 4 to be accommodated between the piston 8 and the outlet opening 5.

The container 2 has an outside diameter of 6.5 mm with a mean wall thickness of 2 mm. The container 2 furthermore has annular enlargements of the outside diameter 9, in the region of the outlet opening 5 and of the actuator opening 6 respectively. Given this configuration of the container 2, it is immediately apparent that the cartridge 1 can be used in a standard dispenser (not shown).

The cannula 3 is formed on the container 2 in such a way that it is fluid-connected to the outlet opening 5 to ensure that dental compound emerging from the outlet opening 5 of the container 2 passes directly into the cannula 3. In the initial state illustrated in FIGS. 1 and 2, the cannula 3 extends along the axis 7 and has a total length of 25 mm, wherein the flexible region 3 thereof, which is described below, extends over 20 mm from the outlet opening 10 of the cannula 3. The outlet opening 10 of the cannula 3 has an inside diameter of 0.7 mm and is rounded with a radius of 0.1 mm.

Under standard conditions, the cannula 3 can be deformed plastically solely by the application of manual force, and it is therefore possible to achieve a permanent bend relative to the initial state shown in FIGS. 1 and 2 through an angle of at least up to 65° without buckling of the cannula 3. FIG. 3 shows by way of example how the cannula 3 of the cartridge 1 can be bent manually or solely by means of fingers 90. Here, the bend is permanent, i.e. is maintained even when the fingers 90 are removed. At the same time, bending up to 65° takes place completely without buckling, i.e. there are no significant changes in shape, due to buckling for example, over the entire length of the cannula 3. Only the area of the internal cross section of the cannula 3 resulting from the inside diameter in the initial state may be reduced by bending—depending on the bending angle—by up to a maximum of 5%.

The cartridge 1 is suitable for high-viscosity dental compounds with a dynamic viscosity of over 27,000 Pa s, at a shear stress of 9,000 N/m², a shear rate of 0.3 1/s and a temperature of 23° C. In particular, the dental compound can be an aqueous astringent retraction paste containing clay minerals and corrosive astringents, the proportion of fillers in which is greater than 50% by weight and which contains HCl as a strong acid ($pK_s \leq 2$). Since the cannula 3 in the cartridge 1 according to the invention does not need to comprise metal either, corrosion problems are avoided.

As already stated, the cartridge 1 illustrated in FIGS. 1 to 3 is designed for standard dispensers, which can apply a maximum squeezing force of 200 N. In terms of its shape but also by means of the material used (see above), the cannula 3 is here matched to the retraction paste described above in such a way that the bent cannula 3 (cf. FIG. 3) makes a return movement of at most 1° during discharge of the high-viscosity dental compound. In other words, therefore, the bend in the cannula 3 produced manually beforehand remains substantially dimensionally stable, even during the discharge of dental compound through the cannula 3.

The invention claimed is:

1. A system comprising: an astringent retraction paste; and a cartridge for storing, discharging, and applying the astringent retraction paste, the cartridge comprising a container (2) having a hollow chamber (4) accommodating the astringent retraction paste, and a cannula (3),
    wherein the hollow chamber (4) comprises an outlet opening (5) and an actuator opening (6) on a side of the hollow chamber opposite the outlet opening (5), wherein the cannula (3) is fluidly connected to the outlet opening (5),
    wherein the cannula (3) is formed integrally with the container (2), the cannula (3) and the container (2) are made of a thermoplastic with a bending modulus within a range of 2.2 to 2.9 GPa at 23° C. in accordance with DIN EN ISO 178:2013,
    wherein the cannula (3) has an outlet opening (10) at an outlet end of the cannula (3) and has an inside diameter within a range of 0.4 mm to 2 mm and a flexible region with a length within a range of 15 mm to 25 mm; and
    wherein the cannula (3) is plastically deformable to bend between a straight state and an angled state by an angle of at least 65° without buckling the cannula (3), wherein the astringent retraction paste includes a dynamic viscosity over 27,000 Pa-s at a shear stress of 9,000 N/m2, a shear rate of 0.3 1/s at a temperature of 23° C.; wherein the astringent retraction paste is configured to be dispensed from the hollow chamber (4) through the cannula (3) in the angled state with a squeezing force of 130 N, and in response to the cannula is configured to move no more than 10°.

2. The system of claim 1, characterized in that the outlet opening (5) and the actuator opening (6) of the hollow chamber (4) lie on a common axis (7).

3. The system of claim 1, characterized in that the thermoplastic contains pigments and/or fillers.

4. The system of claim 3, characterized in that proportion of pigments and/or fillers is less than 50% by weight.

5. The system of claim 1, characterized in that a piston (8) is provided in the hollow chamber (4), and the astringent retraction paste is accommodated in the hollow chamber (4) between the piston (8) and the outlet opening (5).

6. The system of claim 1, wherein the outlet end of the cannula (3) is rounded.

7. The system of claim 1, characterized in that the container (2) is substantially tubular, has an outside diameter of from 6 mm to 7 mm, and has a wall thickness of at least 0.5 mm.

8. The system of claim 1, characterized in that the container (2) has an annular enlargement of the outside diameter (9) in the region of the outlet opening (5) and/or of the actuator opening (6).

9. The system of claim 1, characterized in that the hollow chamber (4) of the container (2) is filled substantially by the astringent retraction paste.

10. The system of claim 9, characterized in that the astringent retraction paste comprises a liquid and a proportion of fillers greater than 50% by weight.

11. The system of claim 9, characterized in that the astringent retraction paste contains a strong acid ($pK_s \leq 2$).

12. The system of claim 11, characterized in that astringent retraction paste contains HCl.

13. The system of claim 1, characterized in that astringent retraction paste is configured to be dispensed from the hollow chamber through the cannula in the angled state, and in response the cannula is configured to move no more than 5°.

14. The system of claim 1, characterized in that thermoplastic is selected from the group of an amorphous thermoplastic copolymer, a terpolymer, and quadropolymer.

* * * * *